United States Patent [19]

Stewart

[11] Patent Number: 4,834,115
[45] Date of Patent: May 30, 1989

[54] PENILE CONSTRICTOR RING

[76] Inventor: Edward T. Stewart, 107 Plaza Ter., Dodge City, Kans. 67801

[21] Appl. No.: 64,503

[22] Filed: Jun. 22, 1987

[51] Int. Cl.[4] .................................................. A61F 5/41
[52] U.S. Cl. .................................... 128/842; 128/79; 128/885; 128/DIG. 25
[58] Field of Search ............. 128/138 R, 79, DIG. 25, 128/774; 604/133

[56] References Cited

U.S. PATENT DOCUMENTS

| 723,259 | 3/1903 | Fraser | 128/138 R |
|---|---|---|---|
| 745,264 | 11/1903 | Todd | 128/138 R |
| 1,748,227 | 2/1930 | Hyams | 128/138 R |
| 3,149,629 | 9/1964 | Katz | 128/79 X |
| 3,675,657 | 7/1972 | Gauthier | 128/138 RX |
| 4,139,007 | 2/1979 | Diamond | 128/138 R |
| 4,222,377 | 9/1980 | Burton | 128/DIG. 25 |
| 4,256,093 | 3/1981 | Helms et al. | 128/DIG. 25 X |
| 4,515,166 | 5/1985 | Timm | 128/774 X |

FOREIGN PATENT DOCUMENTS 41783 12/1887 Fed. Rep. of Germany ... 128/138 R
734394 7/1955 United Kingdom ................. 128/79

Primary Examiner—Robert A. Hafer
Assistant Examiner—Kevin G. Rooney
Attorney, Agent, or Firm—Hovey, Williams, Timmons & Collins

[57] ABSTRACT

A penile constrictor ring consisting of a length of elastic material and a latch for securing the ends thereof together to form a ring which may be placed about the penis in constricting relation thereto to inhibit the circulation of blood therein. Electrically actuated release means are provided to release the latch either automatically by the action of a timer after a predetermined time lapse, in order to prevent damage to the flesh of the organ, or in response to the reception of a radio signal from a transmitter held in the hand of the user, in order to allow normal ejaculation at the time of orgasm. An entirely manual release means is also provided as a safety measure in the event of failure of the electrical systems. An applicator tool is also provided for easy application of the latched and stretched ring to the penis.

15 Claims, 2 Drawing Sheets

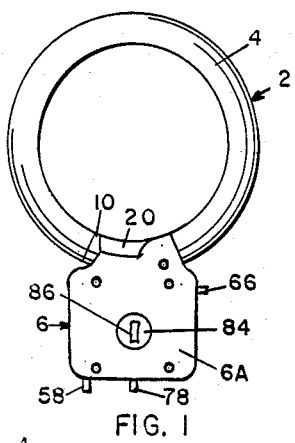
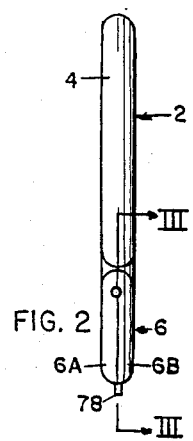
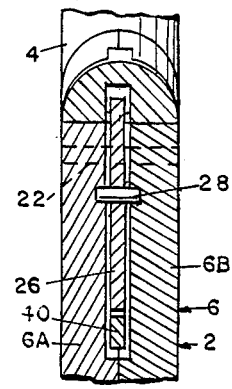
FIG. 1
FIG. 2
FIG. 5
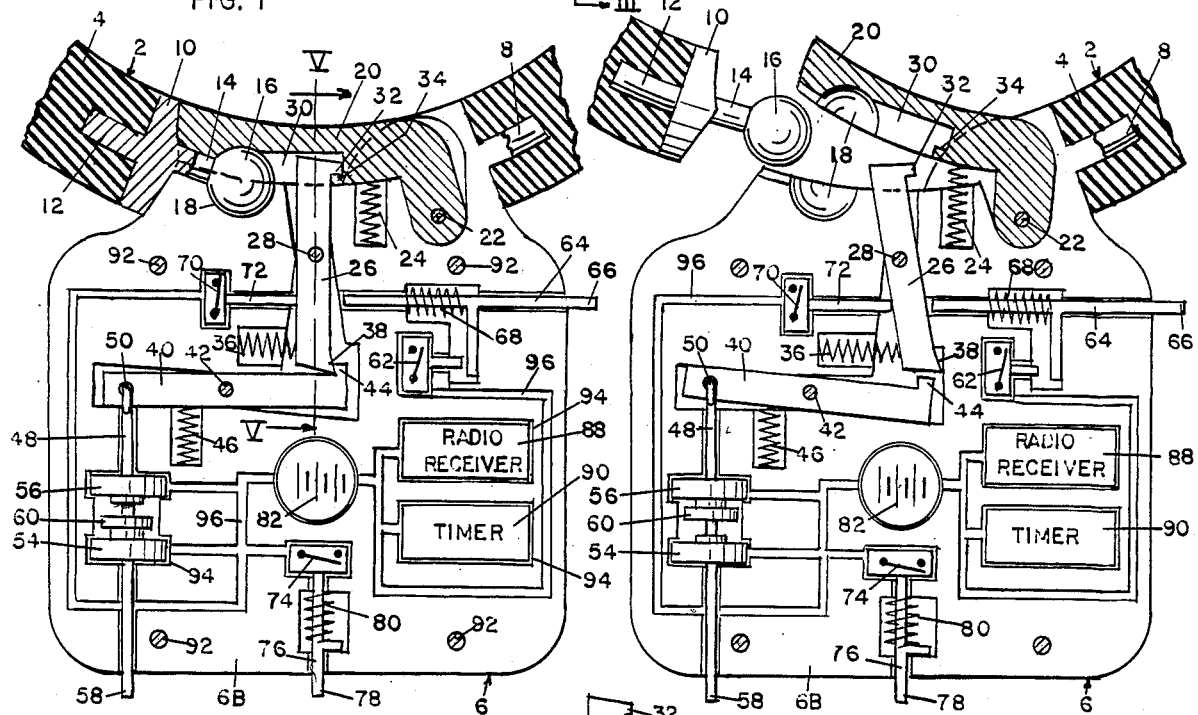
FIG. 3
FIG. 4
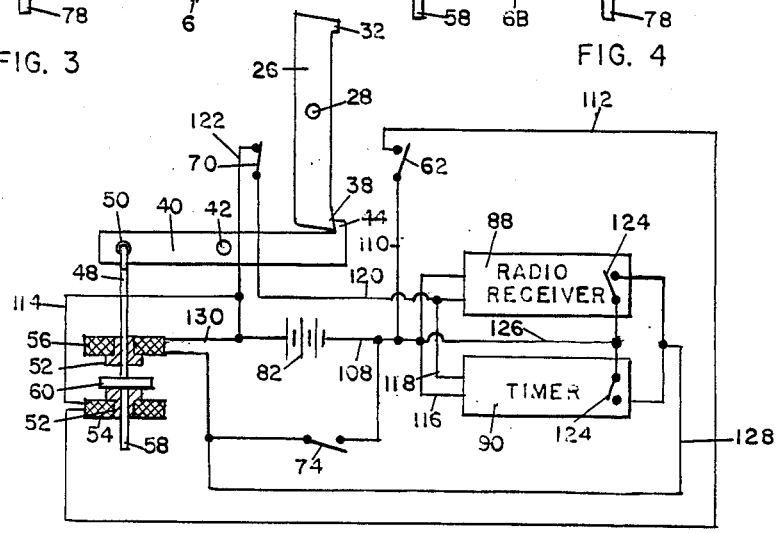
FIG. 6

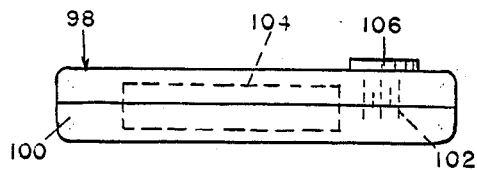
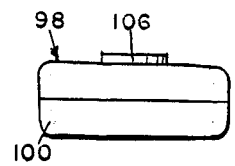
FIG. 7   FIG. 8
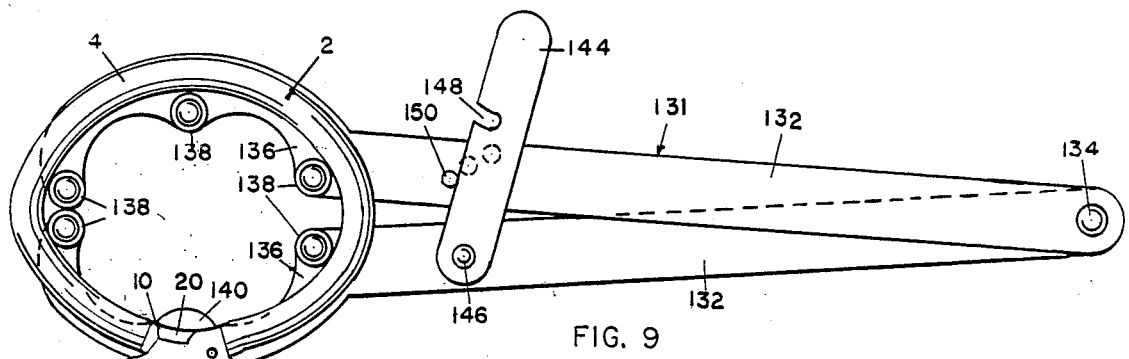
FIG. 9
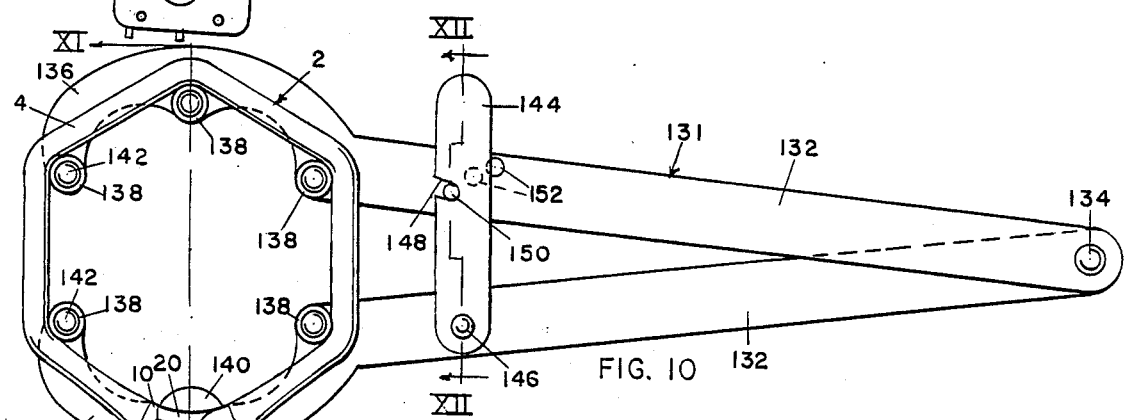
FIG. 10
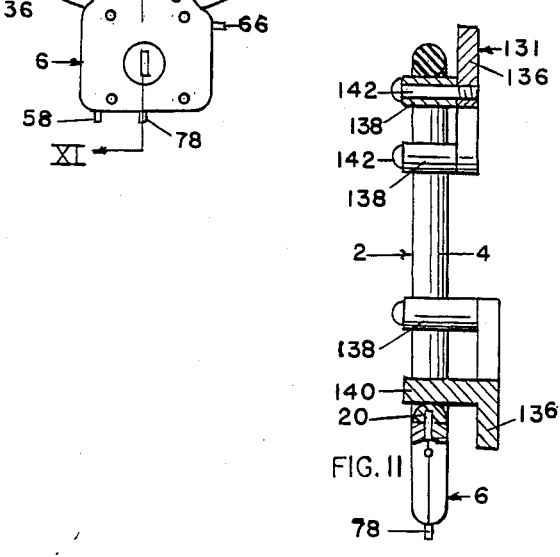
FIG. 11
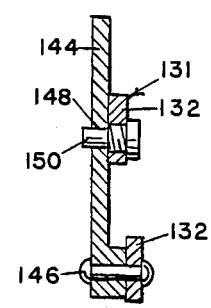
FIG. 12

PENILE CONSTRICTOR RING

This invention relates to new and useful improvements in penile constrictor rings, and has particular reference to both remote and automatic controls for said penile constrictor rings.

BACKGROUND OF THE INVENTION

Penile constrictor rings, consisting generally of an elastic band adapted to encircle the penis closely adjacent the base thereof and adjacent the user's torso, have long been known and used. They have certain well known usages in the treatment of male impotency, when such impotence takes the form of the inability to attain erection in a normal manner, and also when it takes the form of the inability to maintain erection for a sufficiently long period of time to complete a satisfactory act of sexual intercourse. It acts by constricting the flow of blood within the organ in a selective manner, permitting relatively easy flow of blood into the organ while serverely restricting the flow of blood from the organ. This will result in erection of the organ in many cases, and is also effective in permitting longer retention of an erection once it has been obtained. Some cases of impotency may require the use of other devices to obtain original erection, but the constrictor ring will then be effective in retaining the erection as long as may be necessary.

However, penile constrictor rings have in the past been subject to certain well known and even rather notorious defects and disadvantages. First, they may be dangerous to use, in that if left engaged around the penis for unduly long periods of time, they may result in permanent damage to and modification of the flesh of the organ, due to the artificially induced lack of blood circulation therein. They may be very difficult to apply to and remove from the organ, especially if the organ is already erect to partially erect. If applied and fully operative at the moment of orgasm and ejaculation, they interfere with normal ejaculation, and also reduce the pleasurable sensations of orgasm and ejaculation. It is normally almost impossible to interrupt the sex act for removal of the constrictor ring at the moment of orgasm.

SUMMARY OF THE INVENTION

In accordance with the above enumerated shortcomings and disadvantages of the prior art, an important object of the present invention is the provision of a penile constrictor ring consisting of a length of elastic rubber or the like having latch means operable to connect the ends thereof releasably to form a continuous ring for surrounding the penis in constricting relation thereto, the latch means being releasable, whereby to release the penis from constrictive pressure, in response to various signals.

Another object is the provision of a penile constrictor ring of the character described wherein one of the latch release means constitutes an electrically actuated timer operable to release the latch at a predetermined time interval, such as thirty minutes, after it has been engaged, in order to prevent permament damage to the organ due to lack of blood circulation therein. The time interval allowed should of course be determined by competent medical advice, and the thirty minutes mentioned is of course only exemplary. The time should be long enough to permit completion of a normal act of intercourse, but short enough to prevent permanent damage to the organ. This feature combats the tendency of many men to relax and drowse in the pleasurable aftermath of intercourse, which could result in permanent damage if this means of releasing the ring independently of any action of his own were not provided.

A further object is the provision of a penile constrictor ring of the character described wherein another of the latch release means constitutes an electrical radio system including a sender unit which may be conveniently held in the hand of the user during intercourse, and a receiver unit carried in a control box attached to the ring itself, the receiver unit being operable, when actuated, to release the latch. Thus the user may release the latch easily at the very moment of orgasm and ejaculation to avoid interference by the ring with normal ejaculation and the pleasurable sensations accompanying it.

A still futher object is the provision of a penile constrictor ring of the character described which is provided, for safety, with an entirely manually operable latch release means, for use when the electrically actuated release systems fail to function.

Another object is the provision of an applicator tool for applying the constrictor ring to the penis easily and conveniently.

Other objects are comparative simplicity and economy of construction, and ease, convenience and dependability of operation.

BRIEF DESCRIPTION OF THE DRAWING

FIG. 1 is a front elevational view of a penile constrictor ring embodying the present invention, shown latched and of approximately normal size, FIG. 2 is an edge elevational view of the device as shown in FIG. 1, FIG. 3 is an enlarged, fragmentary sectional view taken on line III—III of FIG. 2 with the latch engaged, FIG. 4 is a view similar to FIG. 3, but showing the parts at a moment of latch release, FIG. 5 is a fragmentary sectional view taken on line V—V of FIG. 3, FIG. 6 is a wiring diagram of the device, shown in a condition providing engagement of the latch, FIG. 7 is an edge elevational view of the radio sender unit forming an accessory element of the device, FIG. 8 is an end view of the device shown in FIG. 7, FIG. 9 is a side elevational view of an applicator tool for the constrictor ring, with the constrictor ring initially applied thereto, FIG. 10 is a view similar to FIG. 9, but showing the tool operated to expand the ring for easy application to the penis, FIG. 11 is a sectional view taken on line XI—XI of FIG. 10, and FIG. 12 is a sectional view taken on line XIII—XIII of FIG. 10.

DESCRIPTION OF THE PREFERRED EMBODIMENT

In the drawing, the numeral 2 applies generally to a penile constrictor ring enbodying the present invention. Basically, said constrictor ring comprises a strip 4 of flexible, elastic material, preferably round in cross-sectional contour and formed for example of latex rubber, and a miniaturized, rigid control box 6 interposed between the ends of the strip 4 and projecting outwardly from the loop formed thereby. One end of strip 4 is permanently affixed to control box 6, as shown at 8 in FIGS. 3 and 4, and the opposite end of the strip has a rigid fixture 10 permanently affixed thereto as indicated at 12. Fixture 10 includes a neck 14 projecting generally coaxially with strip 4, and terminating in an enlarged, generally spherical knob 16. Said knob is engageable in the spherical recess 18, one half of which is formed in control box 6 and one half in the free end of a jaw member 20, the opposite end of the jaw member being pivoted in the control box as indicated at 22. When the jaw member is pivoted to its control position, as shown in FIG. 3, knob 16 is secured in recess 18 to close the loop formed by strip 14, but when it is pivoted to its open position, as shown in FIG. 4, the knob may escape from recess 18. The jaw member is biased toward its open position by a spring 24 mounted in the control box. Jaw member 20 may be secured in its closed position by a latch bar 26 pivoted in the control box at 28. One end of said latch bar projects into a cavity 30 formed in the inner surface of the jaw member, and is provided with a laterally projecting tooth 32 which, when the latch bar is pivoted in a clockwise direction as viewed in FIGS. 3 and 4, engages a shoulder 34 of the jaw member to secure the latter in its closed position, but which when the latch bar is pivoted in a counter-clockwise direction disengages said shoulder to permit the jaw member to be opened by spring 24. The latch bar is biased toward its disengaged position by a spring 36 carried in the control box. The latch bar is provided at its opposite end, within the control box, with a bevelled, laterally projecting tooth 38.

Latch bar 26 may be secured in its engaged position by a lock lever 40 pivoted intemediate its ends in the control box, as at 42, and extending generally at right angles to the latch bar. The lock lever is provided at one end with a lateral tooth 44 which, when the lever is pivoted in a counter-clockwise direction as viewed in FIGS. 3 and 4, engages tooth 38 of the latch bar to secure the latch bar in its engaged position, but which when the lever is pivoted in the opposite direction disengages the latch bar to permit it to be moved to its disengaged position by spring 36. The lock lever is biased toward its disengaged position by a spring 46. At the end of lever 40 opposite from tooth 44, a push rod 48 of non-magnetic material such as brass is pivoted thereto as at 50. Said push rod projects slidably through the iron cores 52 of a pair of electromagnets 54 and 56, and projects outwardly from the control box to form a pushbutton 58. Mounted on the push rod intermediate the two electromagnets is a ferrous armature 60. When magnet 54 is energized, armature 60 is drawn downwardly (as shown) and push rod 48 pivots lock lever 40 to its engaged position, and when magnet 56 is energized armature 60 is moved upwardly to move lock lever 40 to its disengaged position. The lock lever may also be moved to its disengaged position by direct manual pressure on pushbutton 58.

Also mounted within the control box is a first normally open electric switch 62 operable to be closed by a push rod 64 slidable in the control box and entending outwardly therefrom to form a pushbutton 66. Rod 64 is biased outwardly by a spring 68, but inward pressure on pushbutton 66 will close switch 62, and also will pivot latch bar 26 to its engaged position. Another normally open electric switch 70 is operable to be closed by a push rod 72 as latch bar 26 is moved to its engaged position. A third normally open electric switch 74 is operable to be closed by a push rod 76 extending outwardly from the control box to form a pushbutton 78. This push rod is biased outwardly by a spring 80, but inward pressure on pushbutton 78 functions to close the switch. Additionally included in the control box are a small electric battery 82 mounted beneath a screw cap 84 provided with a screwdriver slot 86 in order to be accessible for replacement when necessary, a miniaturized radio receiver 88 which is battery powered and is operable to deliver a surge of battery current whenever it receives a signal from a suitable radio transmitter, and an electric timer 90 of a type operable after a predetermined time interval following its energization to deliver a surge of battery current, and to reset its timing cycle each time it is de-energized. Preferably, control box 6 is divided in the plane of the loop formed by strip 4 into two halves 6A and 6B, held in assembly by four screws 92 or the like, with the various components contained thereby disposed in suitable recesses 94, and the wiring (to be described) disposed in suitable passages 96, formed in the mating surfaces of said halves.

FIGS. 7 and 8 show a radio transmitter unit 98 suitable for use with the constrictor ring assembly. It consists of a small case 100 small enough to be held conveniently and unobtrusively in the hand of a user during sexual intercourse, and containing an electric battery 102, a radio transmitter 104 powered by the battery, and a manually operable pushbutton 106. Whenever the pushbutton is depressed, transmitter 104 is actuated to emit a signal suitable to to be responded to by receiver 88 of the control box. This unit is common and is not believed to require detailed description.

The constrictor ring is readied for use by manually disposing knob 16 of fitting 10 between the halves of recess 18 of the control box and jaw member 20, and manually pressing the jaw member closed to secure the knob in the recess. Then, while holding the jaw member closed, the user depresses pushbutton 66. This causes push rod 64 to pivot latch bar 26 to a closed position against the bias of spring 36, whereby its tooth 32 engages shoulder 34 of the jaw member, so that the jaw member is secured closed, and also closed switch 62. Closure of this switch completes an operating circuit from battery 82 through wires 108 and 110, switch 62, wire 112, electromagnet 54, and wire 114 back to the battery. Magnet 54, thus energized, draws armature 60 in a direction such that push rod 48 pivots lock lever 40 to engage its tooth 44 with tooth 38 of the latch bar to secure the latch bar in its engaged position. Pushbutton 66 may then be released. This de-energizes electromagnet 54, but the teeth 38 and 44 of latch bar 26 and lock lever 40 remain engaged, against the disengaging bias of spring 46, due both to the matching bevel of said teeth, which resists disengagement, and also to the fact that the engagement of said teeth is yieldably loaded against disengagement by spring 36. Such teeth may thereafter be disengaged only by the energization of magnet 56, or by manual pressure on pushbutton 58.

The movement of latch bar 26 to its engaged position will then also have acted through push rod 72 to close switch 70, and it will of course remain closed so long as the latch bar remains in its engaged position. The closure of this switch completes a circuit from battery 82 through wires 108 and 116 to radio receiver 88 and timer 90, wires 118 and 120, switch 70 and wire 122 back to the battery. The radio receiver is thus readied for an activating signal from radio transmitter unit 98, and the timer is actuated to start its timing sequence in progress. This condition will prevail so long as switch 70 remains closed. Radio receiver 88 and timer 90 each include a normally open switch 124, to one terminal of each of which battery current is furnished by wire 126, and each of which is operable to be closed by the device in which it is contained. That is, the switch 124 in radio receiver 88 is operable to be closed in response to the reception by the receiver to a signal from radio transmitter 98, generated whenever pushbutton 106 of the transmitter is pressed, and the switch 124 in timer 90 is operable to be closed by the timer whenever the time interval for which the timer is preset expires. Whenever either of these events occurs, battery current from the appropriate switch 124 is delivered through wires 128, electromagnet 56 and wire 130 back to the battery. Magnet 56, thus energized, draws armature 60 toward magnet 56, and acting through push rod 48 pivots lock lever 40 to disengage its tooth 44 from tooth 38 of latch bar 26. This pivotal motion of the lock lever is assisted by spring 46, and overcomes spring 36 and the resistance to disengagement offered by the bevel of the teeth. Latch bar 26, thus released, is pivoted in a counter-clockwise direction to free its tooth 32 from the shoulder 34 of jaw member 20, and the jaw member is pivoted by spring 24 to free knob 26 from recess 18, and the tension of rubber strip 4 around the penis is totally released. Actually, if inward pivoting of the jaw member is blocked by direct engagement thereof with the penis, the entire control box 6 may pivot outwardly, generally about pivot 22 as an axis, to allow escape of knob 16 from recess 18. After the ring has been fully latched as described above, it is stretched and fitted about the penis at its root, closely adjacent the user's body, and it is of such size that when then released, it will contract to apply constrictive pressure on the penis, as discussed above. That is, if properly sized to the organ of a user, it will tend to allow the flow of blood into the organ through the arteries, which are relatively deeply seated in the organ, but to prevent outward flow of blood from the organ through the veins, which are disposed relatively close to the surface of the organ. In most cases, this will produce an erection of the organ. In relatively rare cases, however, other means may be required to produce an initial erection before the constrictor ring is applied, the constrictor ring then functioning to maintain the erection. Some men are capable of producing an erection, but incapable of maintaining it for a sufficient time to complete a satisfactory act of intercourse. One means for producing an initial erection, when the constrictor ring cannot, is a device for subjecting the penis to a vacuum, which encourages blood to rush to the organ to encourage erection, such as shown in my copending application Ser. No. 07/014,361, and after or even during the application of such vacuum the present constrictor ring may be applied.

The user may release the constrictor ring at any time during intercourse by pressing pushbutton 106 of radio transmitter 98, which releases the ring as described above. He may do so, for example, at the moment of orgasm and ejaculation, in order to heighten the pleasurable sensations of orgasm, and to avoid interference by the ring with normal ejaculation. He may also release the ring in the event he should suffer pain or discomfort during intercourse. He should be carefully instructed to release the ring under these circumstances, since such pain or discomfort may signal the possibility of damage to the penis. If he does not use the remotely controlled radio release, there is the possibility that he may doze or drowse off in the relaxed, pleasurable aftermath of intercourse with the constrictor still in place. If he does so, timer 90 will automatically release the ring after its preset time interval, also as described above. This is very important, since the continued subjection of the penis to the abnormal restriction of blood circulation in the organ, as caused by the constrictor ring, may very well then result in permanent and irreversible damage to the organ.

The depression of pushbutton 106 also provides a valuable means for testing the operability of the release system, and it should be depressed after the ring is latched, but before the ring is applied to the penis, in order to make sure that release does occur. If it does not, it may indicate faults in the radio transmission and reception system, or that battery 82 is weak and should be replaced, or that electromagnet 56 is not functioning properly. The device should of course not then be used until the fault has been corrected. Depression of pushbutton 78 closes switch 74, which completes an operating circuit for electromagnet 56 independently of the radio system, and this may serve to further pinpoint any fault causing non-release. Of course, if battery 82 is too weak to cause proper functioning of electromagnets 54 and 56, the ring will not lock in its latched position at all, since magnet 54 will not then function to pivot lock lever 40 to its locking position, and jaw member 20 will immediately spring open when pushbutton 66 is released. If in actual use release of the ring fails to occur in response to pressure on pushbutton 106, or for that matter to pressure on pushbutton 78, the user may effect release by pressure on pushbutton 58, which releases the latching and locking means entirely manually, independently of any electrical system. The use of pushbutton 78 and switch 74 is largely optional, since it primarily serves only a test function, but the totaly manual release system provided by pushbutton 58 is considered to be a necessary safety precaution.

It is entirely possible, after the ring has been initially latched and locked, to expand the ring and apply it to the penis as described entirely manually. Expansion is necessary since the ring must contract and constrict the penis when applied, and the expansion may require considerable force. It should be noted that the ring must be sized to the organ dimensions of each separate user in order to apply the correct degree of constriction when thus applied. Testing has shown that rings of about seven different unstretched diameters will provide an adequate range such that one of them will properly accomodate the organ of nearly any male. The proper size should of course be selected with competent medical advice. However, manual stretching and application of a latched constrictor ring is somewhat awkward and tedious, whether the penis is erect or not, as is the proper placement of the ring at the base of the penis. The operation is greatly facilitated by an applicator tool 131 such as shown in FIGS. 9–12 of the drawing. Said tool comprises a pair of elongated arms 132 pivotally connected together at one pair of corresponding ends, as at 134, and having confronting, generally semi-circular jaws 136 at their opposite ends. Each of said jaws has a plurality, three shown, of rollers 138 mounted thereon for rotation about axes transverse to the plane of said jaws, except that one of said rollers, the middle roller of the lower jaw, is replaced by a laterally extending finger 140 the outer surface of which is configured to engage the jaw member 20 of the control box 6 of a latched constrictor ring when said ring is applied to the tool as shown in FIG. 9. Each roller comprises a tubular member rotatably mounted on a headed pin 142 fixed in its associated jaw 136. The rollers, and finger, are so arranged on the jaws that when the jaws are separated to the extent shown in FIG. 10, they define the corners of an approximately hexagonal shape, but when the jaws are moved as close to each other as possible, as shown in FIG. 9, the rollers and finger define a much smaller area. The spacing of the arms 132, and hence of jaws 136, may be secured by a latch bar 144, which is pivoted at one end, as at 146, to one of arms 132, and is extended to intersect the other of said arms. A notch 148 is formed in an edge of the latch bar and is adapted to engage over a pin 150 fixed in the other arm, whereby to fix the spacing of the arms. Pin 150 is threaded, as indicated in FIG. 12, for selective engagement in any one of a series of holes 152 formed therefor in its associated arm, whereby the fixed spacing of the arms may be varied.

The tool 131 is used by first collapsing arms 132 to their minimum spacing, as shown in FIG. 9, then applying a previously latched constrictor ring 2 over rollers 138 and finger 140 as shown. This may be done easily and conveniently, since it requires relatively little stretching of the elastic strip 4. Finger 140 serves to hold the control box 6 in position. The jaws are then expanded to the position shown in FIG. 10 by manually moving arms 132 apart until pin 150 can be engaged by notch 148 of latch bar 144, as shown in FIG. 10. Then, using arms 132 as a handle, the restrictor ring, which should be disposed at the side of the jaws 136 toward the user's body, is moved over the head of the penis to a position at the base of the organ, closely adjacent the user's torso. The ring may then be slipped off rollers 138 to engage and constrict the penis as desired. The removal of the ring from rollers 138 may be facilitated by the prior application of petroleum jelly or the like either to the ring itself, or to rollers 138, or both.

While I have shown and described a specific embodiment of my invention, it will be readily apparent that many minor changes of structure and operation could be made without departing from the spirit of the invention.

I claim:

1. A penile constrictor ring comprising:
   a. a strip of elastic material having first and second ends,
   b. latch means operable to join the ends of said strip of elastic material releasably together whereby to form a ring sized to apply constrictive pressure to a penis when placed in encircling relation thereto, and
   c. release means operable to release said latch means including motive means separate from said latch means and operatively associated with said latch means, and energy-storing means separate from said strip and said latch means to allow the release of said latch means from the first end of said strip, said energy-storing means being operatively associated with said motive means for the selective release of said latch means.

2. A penile constrictor ring as recited in claim 1 wherein said release means is manually operable entirely independently of any electric circuit.

3. A penile constrictor ring as recited in claim 1 wherein said latch means comprises a small, rigid control box affixed to one end of said strip and forming relatively movable jaw members, an extension affixed to the opposite end of said strip and terminating in an enlargement operable to be trapped between said jaw members when they are closed, said latch means being operable to secure said jaw members releasably closed, and wherein said release means is carried in said control box and is operable when actuated to release said jaw members.

4. A penile constrictor ring as recited in claim 3 including means in operable communication with and remote from said control box for actuating said release means.

5. A penile constrictor ring as recited in claim 3 wherein said release means includes an electrically actuated device operable when actuated to release said latch means, an operative electric circuit for said device, a normally open first electric switch included in said circuit, and a signal device operable when actuated to close said first switch.

6. A penile constrictor ring as recited in claim 5 wherein said release means is provided with means for manually opening said jaw members independently of any electric circuit.

7. A penile constrictor ring as recited in claim 5 wherein said signal device constitutes:
   a. an electrically operated timer operable a predetermined time interval after it is energized to close said first switch,
   b. an operative electric circuit for said timer,
   c. a normally open second electric switch disposed in said circuit, and
   d. manually operable means operable to close said second switch.

8. A penile constrictor ring as recited in claim 7 wherein said manually operable means for closing said second switch is mechanically responsive to the engagement of said latch means, whereby said timer is actuated only when said latch means is engaged.

9. A penile constrictor ring as recited in claim 5 wherein said signal device comprises a radio receiver operable to receive an actuating radio signal and to respond thereto by closing said first switch, an operative electric circuit for said radio receiver including a normally open second electric switch, and manually operable means operable to close said second switch, and with the addition of a separate hand held radio transmitter device adapted to be held in the hand of the user and operable by manual operation of a sending button thereof to transmit a radio signal to which said radio receiver can respond to close said first switch.

10. A penile constrictor ring as recited in claim 9 wherein said means for closing said second switch is mechanically responsive to the engagement of said latch means, whereby said radio receiver is energized only when said latch means is engaged.

11. A penile constrictor ring as recited in claim 7 with the addition of a second signal device comprising:
   a. a radio receiver operable to receive an actuating radio signal and to respond thereto by closing said first switch,
   b. an operative electric circuit for said radio receiver,
   c. said second electric switch also being disposed in the operating circuit of said radio receiver,
   d. manually operable means for closing said second switch, and with the addition of
   e. a separation hand held radio transmitter device adapted to be held in the hand of the user and operable by manual actuation thereof to transmit a radio signal to which said radio receiver will respond to close said first switch.

12. A penile constrictor ring as recited in claim 11 wherein said means for closing said second switch is mechanically responsive to the engagement of said latch means, whereby said timer and said radio receiver are actuated only when said latch means is engaged.

13. A penile constrictor ring as recited in claim 3 wherein said jaw members are manually closable, and wherein said latch means and said release means comprise:
   a. pivotal latch bar operable when engaged to secure said jaw members closed,
   b. spring means biasing said latch bar to its disengaged position,
   c. a pivotal lock lever operable when pivoted in one direction to secure said latch bar in its engaged position,
   d. spring means biasing said lock lever to its disengaged position,
   e. a first electromagnet operable when energized to pivot said lock lever to its engaged position,
   f. a second electromagnet operable when energized to pivot said lock lever to its disengaged position,
   g. a first normally open electric switch,
   h. a first electric circuit including a source of electric current, said first switch and said first electromagnet,
   i. manually operable means operable both to pivot said latch bar to its engaged position and to close said first switch, whereby said first electromagnet is energized to pivot said lock lever to its engaged position,
   j. second and third normally open electric switches,
   k. an electrically energized timer operable after the passage of a predetermined time after its energization to close said second switch,
   l. an electrically energized radio receiver operable responsively to a suitable radio signal to close said third switch,
   m. a second electric circuit including said source of electric current, said timer, and said radio receiver,
   n. a third electric circuit including said source of electric current, said second and third switches disposed in parallel, and said second electromagnet,
   o. a separate radio transmitter adapted to be held in the hand of the user and operable by manual actuation thereof to transmit a radio signal to which said radio receiver will respond to close said third switch.

14. A penile constrictor ring as recited in claim 13 with the addition of a fourth normally open electric switch disposed in said second electric circuit, said fourth switch being closed mechanically in response to movement of said latch bar to its engaged position, whereby said timer and said radio receiver are energized only when said latch bar is engaged to secure said jaw members closed.

15. A penile constrictor ring as recited in claim 13 with the addition of manually operable means operable to pivot said lock lever to its disengaged position, entirely independently of any electrical system.

* * * * *